Figure 1:
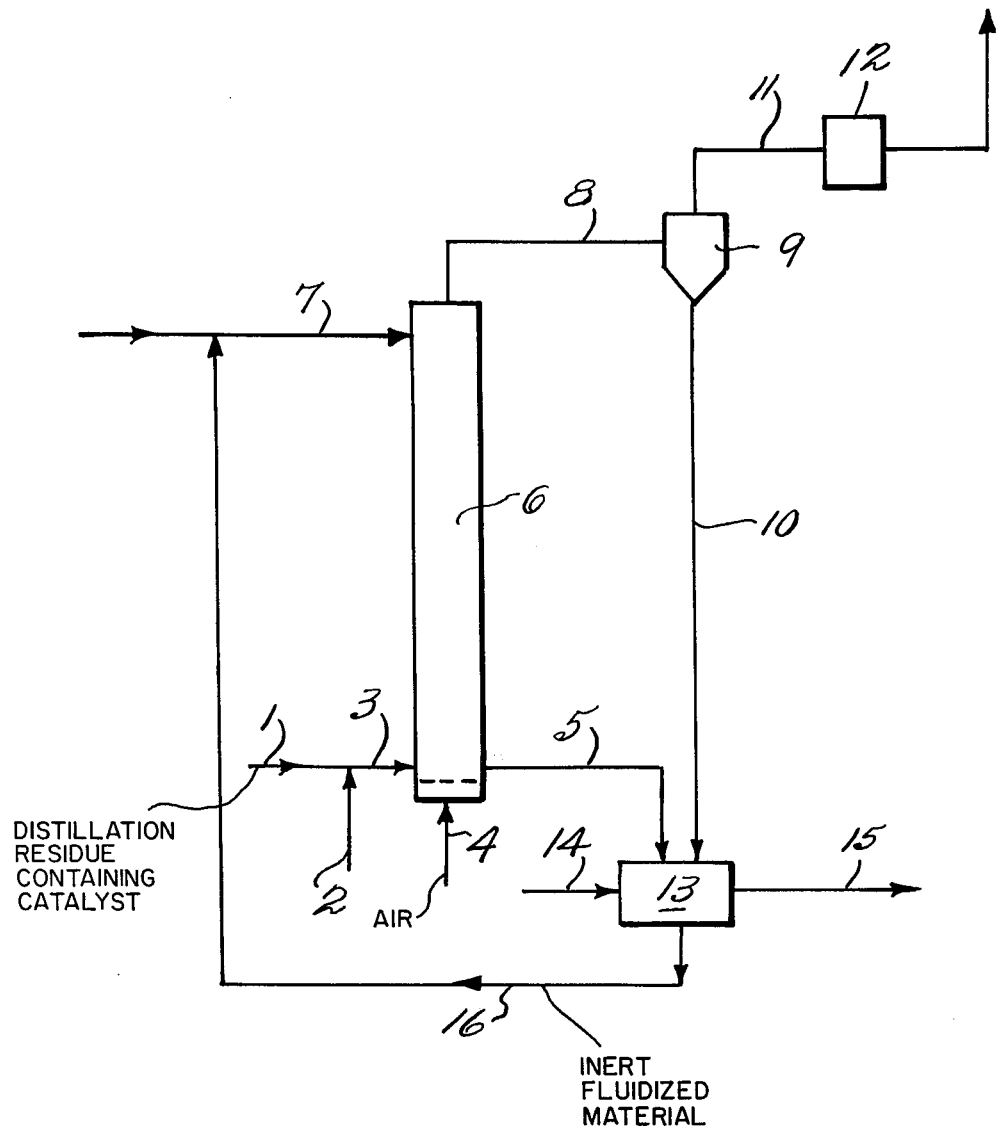

United States Patent [19]

Friedrich et al.

[11] 4,197,161
[45] Apr. 8, 1980

[54] PROCESS FOR THE RECOVERY OF CATALYSTS IN THE EPOXIDATION AND HYDROXYLATION OF OLEFINIC COMPOUNDS

[75] Inventors: Heinz Friedrich, Hanau; Wolfgang Heim, Bruchköbel; Axel Kleemann, Hanau; Heinz Kolb, Hanau; Gerd Schreyer, Hanau, all of Fed. Rep. of Germany

[73] Assignee: Deutsche Gold- und Silber-Scheideanstalt vormals Roessler, Frankfurt, Fed. Rep. of Germany

[21] Appl. No.: 618,236

[22] Filed: Sep. 30, 1975

[30] Foreign Application Priority Data

Nov. 18, 1974 [DE] Fed. Rep. of Germany ....... 2454572
Nov. 18, 1974 [DE] Fed. Rep. of Germany ....... 2454630

[51] Int. Cl.² .............................................. C10G 9/32
[52] U.S. Cl. ..................................... 201/31; 252/417
[58] Field of Search ................ 203/39, 40, 41, 47; 201/12, 31; 210/63 R; 159/DIG. 3; 260/702, 687, 348.5; 252/416, 417, 419, 420; 423/53, 62, 64, 74, 3; 34/10; 110/7 B; 75/121

[56] References Cited

U.S. PATENT DOCUMENTS

| 2,164,826 | 7/1939 | Langwell | 260/348.5 R |
|---|---|---|---|
| 2,649,463 | 8/1953 | Skelly | 260/348.5 R |
| 2,758,073 | 8/1956 | Krebs | 203/41 |
| 2,838,575 | 6/1958 | Smith | 260/687 |
| 3,172,913 | 3/1965 | Hornig | 252/416 |
| 3,240,718 | 3/1966 | Gatsis | 252/416 |
| 3,410,761 | 11/1968 | Slattery | 203/47 |
| 3,562,150 | 2/1971 | Hamilton | 252/416 |
| 3,920,449 | 11/1975 | Onoda | 75/121 |
| 3,926,129 | 12/1975 | Wall | 159/DIG. 3 |
| 3,947,543 | 3/1976 | Thiel | 252/416 |

FOREIGN PATENT DOCUMENTS 2252938 10/1972 Fed. Rep. of Germany .... 260/348.5 L

OTHER PUBLICATIONS

Condensed Chemical Dictionary, Hawley Van Nostrand Reinhold Co., 8th Ed. 1971, N.Y. p. 882.

Primary Examiner—Hiram H. Bernstein
Attorney, Agent, or Firm—Cushman, Darby & Cushman

[57] ABSTRACT

Catalysts used in the epoxidation or hydroxylation of water soluble olefinic compound with hydrogenperoxide are recovered by separating the catalyst as a distillation residue, the distillation residue is introduced into an inert material which is in whirling movement, e.g., as a fluidized bed, the organic compounds contained in the distillation residue are burned with oxygen or oxygen containing gases whereupon the catalyst compound separated on the inert whirling material together with the portion of the catalyst compound which accumulates in the solids separator connected at the outlet of the reactor is dissolved in water and the solution obtained again used for epoxidation or hydroxylation.

28 Claims, 2 Drawing Figures

PROCESS FOR THE RECOVERY OF CATALYSTS IN THE EPOXIDATION AND HYDROXYLATION OF OLEFINIC COMPOUNDS

It is known that compounds of certain transition metals are especially effective catalysts in the epoxidation or hydroxylation of olefinic compounds.

As has been said, first of all as catalysts for epoxidation and hydroxylation are compounds of transition metals such as zirconium, vanadium, niobium, tantalum, chromium, molybdenum, tungsten, rhenium and uranium.

These catalysts are frequently used in the form of their salts and also as metallo-organic compounds. If they are used as organic compounds the catalysts are frequently added in the presence of basic components such as lithium, sodium, potassium, rubidium, cesium, magnesium, calcium, strontium or barium, see Kollar U.S. Pat. No. 3,351,635, the entire disclosure of which is hereby incorporated by reference and relied upon.

However, there are also used heteropolyacids of elements of Group VI of the periodic table, see Smith U.S. Pat. No. 2,754,325, the entire disclosure of which is hereby incorporated by reference and relief upon.

As oxidizing agents there are used for example organic peroxides, e.g., t-butyl peroxide, benzoyl peroxide, hydroperoxides, e.g., t-butyl hydroperoxide and cumene hydroperoxide, and hydrogen peroxide.

More specifically it is known to epoxidize or hydroxylate water soluble olefinic compounds, e.g., allyl alcohol or crotyl alcohol, with hydrogen peroxide using compounds of transition metals as catalysts. Thus compounds of vanadium, molybdenum and tungsten are suited for this purpose. Especially preferred for the epoxidation are tungsten compounds. Since the catalysts are a major factor in the economics of the process because they are expensive, there are a number of known processes for the recovery of tungsten containing catalysts.

Thus there result in the epoxidation or hydroxylation of allyl alcohol to glycide or glycerine acqueous reaction solutions from which the catalyst must be recovered.

According to the process of Anderson, U.S. Pat. No. 2,869,986, tungstic acid is adsorbed on alumina from an acid solution at a pH not greater than 3. The adsorbed tungstic acid can be recovered with sodium hydroxide solution whereby the alumina is simultaneously regenerated. However, the tungstic acid must again be isolated from the regeneration solution by precipitation with strong acids ($HNO_3$, HCl, $H_2SO_4$) wherewith in all there is a relatively large expense for recovery of the catalyst. The entire disclosure of Anderson is hereby incorporated by reference and relied upon.

In place of alumina there have also been employed ion exchangers, e.g., ion exchange resins as shown in German Auslegeschrift 1,114,468 and related Baker U.S. Pat. No. 2,968,527. The entire disclosure of Baker is hereby incorporated by reference and relied upon. In the process of the Auslegeschrift and Baker the tungstic acid is precipitated from the eluate with strong acids.

After the hydroxylation of allyl alcohol the tungstic acid can be removed from the glycerine solution by addition of calcium chloride to the glycerine solution. The tungstic acid dissolved in the glycerine solution is precipitated with formation of the insoluble calcium tungstate and separated. In the recovery of the tungstic acid, here also there must be used precipitation with acids, see Markina German Auslegeschrift No. 1,230,000.

By the precipitation of tungstic acid with strong acids from aqueous tungstate solutions, however, the waste water becomes strongly loaded with salt.

All of the above-named processes additionally have the disadvantage that the catalyst cannot be recovered quantitatively.

In the processes for the catalytic epoxidation and hydroxylation of olefinic compound there accumulates distillation residues which contain high boiling, for the most part polymeric, organic compounds as well as the catalyst compounds. These high boiling organic compounds are not able to be used industrially and must therefore be destroyed. Since with the above-named catalysts there are employed compounds which contain valuable metals, the recovery of these metals is of great importance.

The burning of the organic compounds of the distillation residue in the presence of catalysts in a normal combustion furnace leads to considerable difficulties which make it practically impossible to utilize such a combustion, see German Offenlegungsschrift 2,252,938 and related Levine U.S. Pat. Nos. 3,819,663, e.g., column 3, lines 41–46. (The entire disclosure of Levine is hereby incorporated by reference and relied upon.)

Therefore according to this Offenlegungschrift and Levine, the catalyst containing distillation residue is subjected to a wiped film evaporator on the one hand to obtain the preponderant amount of the organic components in a burnable form and on the other hand to separate off substantially all of the catalyst.

An evaporator so constructed is subjected to a relatively high wear whereby foreign metals go into the discharged solids and which can be extracted with the separated catalyst. The foreign metals are enriched with time to such an extent that it is no longer possible to recycle the catalyst. Besides the thus discharged solids still contain carbonized material which is still partially soluble in the extraction of the catalyst, e.g., with water or organic solvents and can lead to considerable disturbances in the subsequent reuse of the catalyst.

Therefore one of the problems of the present invention was to obtain a complete recovery of the metals from the catalyst compounds as well as environmentally favorable destruction of the high boiling, mostly polymeric compounds contained in the distillation residue in the catalytic epoxidation or hydroxylation of olefinic compounds. Such olefinic compounds include, for example, any of those mentioned in the aforementioned patents, e.g., allyl alcohol, crotyl alcohol, propylene, ethylene, n-butylene, isobutylene, the pentenes, methyl pentene, the hexenes, the octenes, decene-1, dodecine-1, isoprene, cyclohexene, methylcyclohexene, cyclohexadiene, butadiene, styrene, methyl styrene, vinyl toluene, vinyl cyclohexene, methallyl alcohol, diallyl ether, methyl oleate, geraniol, cyclohexenol, cinnamyl alcohol, methyl vinyl ether, methyl methacrylate allyl chloride, oleyl alcohol, methyl vinyl ketone, linseed oil, olive oil, 1,2,3,4,10,10-hexachloro-1,4,4a,5,8,8a-hexahydro-1,4,5,8-endo, exodimethanonaphthalene, soybean oil, cottonseed oil, tall oil, corn oil, castor oil, ethylene-propylene copolymer, hexadecene-1, acrylic acid, crotonic acid, sorbic acid, maleic acid, allyl acetate, oleyl acetate, acrolein.

As catalyst compounds for the epoxidation or hydroxylation there can be used any of those mentioned in the aforementioned patents, e.g., selenotungstic acid, sulfotungstic acid, molybdotungstic acid, tungstic acid, molybdenum naphthenate, molybdenum hexacarbonyl, phosphomolybdic acid, molybdenum trioxide, titanium naphthenate, tungsten carbonyl, rhenium heptoxide, columbium naphthenate, tetrabutyl titanate, a mixture of molybdenum naphthenate and sodium naphthenate, tungstic oxide, sodium tungstate.

Likewise there can be used any of the peroxy compounds set forth in the above-identified patents, e.g., hydrogen peroxide, cumene hydroperoxide, t-butyl peroxide, t-butyl hydroperoxide, benzoyl peroxide, ethylbenzene hydroperoxide, cyclohexanone peroxide, tetralin hydroperoxide, methyl ethyl ketone peroxide, alpha phenylethyl hydroperoxide.

According to one aspect of the invention the residue resulting after distillation of the epoxidation or hydroxylation products, which residue contains high boiling organic compounds and the transition metal catalyst is introduced into an inert material which is in whirling movement, e.g., as a fluidized bed, the organic compounds contained in the distillation residue are burned with oxygen or oxygen containing gases and the metal compounds of the catalyst deposited on the inert whirling material or in the solids separator connected at the outlet of the reactor.

In the preferred form of the invention there is employed a process in which the catalyst, i.e., the usual alkali vanadate, molybdate and tungstate, (see Wiberg, "Anorganische Chemie", 24th and 25th edition, page 476 and 477, the entire disclosure of these pages of Wiberg being hereby incorporated by reference and relied upon) is again added without previous precipitation.

According to this preferred procedure, the residue resulting after the distillation of the epoxidation or hydroxylation products, which residue contains the catalyst is introduced into an inert solid material which is in whirling movement, e.g., as a fluidized bed, the organic components in the distillation residue burned with oxygen or oxygen containing gases, whereupon the catalyst compound separated on the fluidized bed material together with the portion of the catalyst compound which accumulates in the solids separator connected at the outlet of the reactor is dissolved in water and the solution obtained is again used for epoxidation or hydroxylation.

The catalyst thus resulting from the distillation residue can, also, as above-stated, be added without further for the epoxidation or hydroxylation.

Alkali salts of the above-named metals include the sodium, potassium and lithium compounds, preferably sodium compounds. Such compounds include for example sodium tungstate, sodium vanadate, sodium hydrogen tungstate, sodium hydrogen molybdate, sodium molybdate, potassium tungstate, potassium vanadate, potassium hydrogen vanadate, sodium hydrogen vanadate, potassium molybdate, lithium tungstate, lithium vanadate and lithium molybdate. As whirling material there can be used any hard, chemical inert material, as for example, quartz sand (silica sand), silicon carbide, highly fired alumina (e.g., corundum) and highly fired clay (for example chamotte). The particle size is usually 0.1–5 mm, preferably 0.5–1.5 mm.

As fluidized reactor there can be used a reactor of any construction. It can be so constructed that there can take place continuous or discontinuous exchange of the fluidized bed material laden with catalyst in the reactor against fresh fluidized bed material according to two methods in principle. According to the first method a specific amount of the fluidized bed material laden with catalyst is carried out continuously or discontinuously from the lower part of the reactor. About simultaneously there is added into the fluidized reactor continuously or discontinuously the same amount of fresh fluidized bed material.

According to the second method the fluidized reactor is provided with an overflow whereby according to the continuous or discontinuous addition of fresh fluidized material the same amount of fluidized material the preponderant portion of which is laden with the catalyst is discharged continuously or discontinuously by way of the overflow, e.g., in a cyclone connected to the outlet thereof.

Besides pure oxygen there can be employed other oxygen containing gases, especially air. The amount of gas used must be so regulated that the fluidization of the entire particle spectrum of the fluidized material is guaranteed.

Should, as is strived for unlimitedly to protect the environment, the burning of the organic components of the distillation residue be complete in the fluidized bed reactor, i.e., the waste gas is nearly free of carbonmonoxide, then simultaneously the maximum amount of product throughput is established by the above given amount of gas.

The gas can in a given case be preheated, e.g., by the hot waste gas.

As solids separator there can be employed customary apparatus such as gravity separators or cyclones or dust filters.

The reactor temperature is between 500 and about 1,000° C. or between 500° C. and the melting point of the corresponding catalyst compounds (or between 500° C. and the melting point of the inorganic metal containing compounds formed in the combustion, i.e., oxides or salts) if these are below 1,000° C.

The reactor temperature is regulated by cooling with customary cooling devices and cooling means and held constant. Thereby the excess heat of combustion led off through the cooling agent can be used for the production of energy, e.g., for the production of steam or to operate a turbine. As excess heat of combustion is designated the heat which remains after drawing off the amount of heat necessary for the heating of the added materials to the reaction temperature and after removal of the amount of heat radiated by the reactor.

Cooling devices can be, for example, the wall of the reactor and cooling tubes or cooling plates inserted in the fluidized bed. As cooling agents there can be used for example the known nitrite-nitrate melts, e.g., sodium nitrite-sodium nitrate, potassium nitrite-potassium nitrate and mixtures thereof.

The off gas which contains the solids particles is led over a known solids separator, preferably a cyclone, connected to the reactor. The preponderant amount of the entrained solids are separated in the separator. Subsequently the off gas can, if desired, be given a further purification in known manner, while the fine dust also not separated in the solids separator (particle sizes below about 10–30μ) are separated, e.g., by a filter or by a wet wash with water.

In the preferred form of the invention the discharged fluidized material and the material separated in the solids separator or separators are combined and treated with water or aqueous solution from the off gas wash.

Preferably the amount is adjusted according to the desired concentration of the solution to be returned to the epoxidation or hydroxylation reactor.

The recovered catalyst solution can be returned directly to the reactor.

The distillation residue can be recovered in conventional manner, e.g., with the help of circulation evaporators or thin layer evaporators.

The metal compounds of the catalyst accumulate almost completely on the fluidized material and in the solids separator. The type of change required for the metal compounds recovered into fresh catalyst depends on the type of catalyst to be recovered. Several procedures are given in the examples. With the preferred catalysts the procedure can be as described above, i.e., simply dissolving the tungsten, molybdenum or vanadium compound in water after the burning of the organic material and separation of the fluidized material.

The preferred process is usable for the epoxidation and hydroxylation of water soluble olefinic compounds, as, for example, allyl alcohol, crotyl alcohol, methallyl alcohol or cyclopentenol-3.

The industrial advantage of the preferred process of the invention is in the quantitative recovery of the catalyst. Besides it is accumulated in such a form that it is again capable of being inserted into the process reactor. The catalyst recovered is practically the same amount as that initially added. Besides the process is favorable to the environment since no salt containing waste water and also no waste air problems occur.

Unless otherwise indicated, all parts and percentages are by weight.

Figure 2:
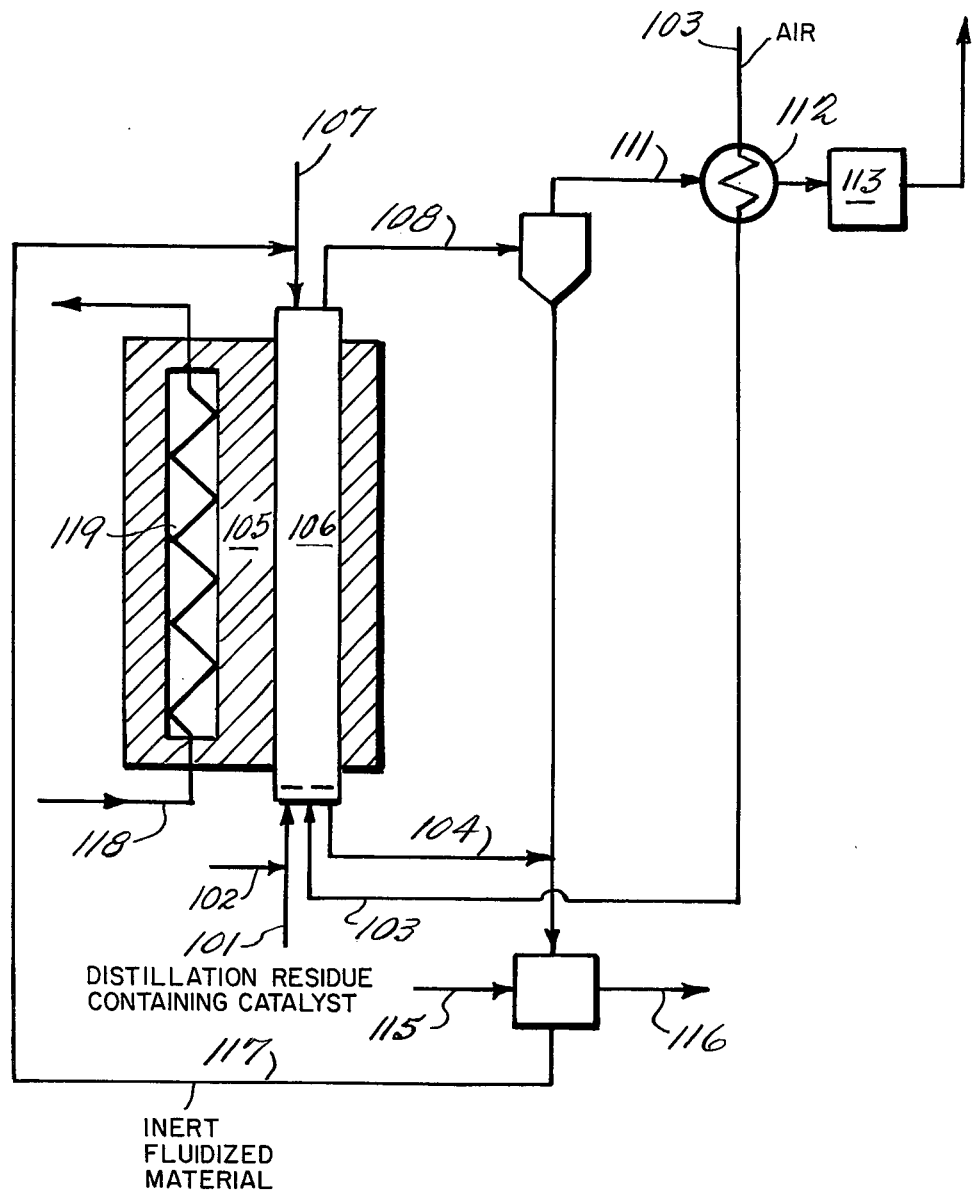

The invention will be understood best in connection with the drawings wherein:

FIG. 1 is a schematic illustration of the preferred process of the invention; and FIG. 2 is a schematic illustration of an alternative process according to the invention.

Referring more specifically to FIG. 1:

The catalyst containing distillation residue is, in case it is not pumpable, brought into a pumpable condition either by heating or by dilution with water or the washing solution from the wet wash.

The catalyst containing distillation residue is then pumped via line 1 into the lower part of reactor 6. Simultaneously air is blown in through line 2 in order to avoid an eventual clogging. The mixture is dosed into the reactor via line 3. The main amount of the air necessary for combustion and fluidization is supplied via line 4 and is optionally preheated.

The reactor is heated to the desired temperature (at least 500° C.). The heating can take place with the help of a starting heater while the fluidized reactor is brought to the necessary temperature for starting the combustion reaction either directly through the hot burned gas or through heated air in the starting heater by heat exchange. After the beginning of the combustion reaction in the fluidized reactor the excess heat of reaction is led off through a cooling system.

Preferably for heating up the fluidized reactor there is employed a salt bath, which for example can be the known nitrite-nitrate melt (sodium nitrite-sodium nitrate). The salt bath in this case serves, after the starting of the reactor, as coolant, because it carries away the heat set free and thus the temperature held at a constant level.

The addition of the material to be fluidized takes place via line 7, the withdrawal together with the catalyst takes place via line 5.

The catalyst containing fluidized material goes into a container 13, where it is washed out with water (supplied via line 14). The aqueous catalyst solution is separated from the fluidized material and can then be led directly via line 15 to the epoxidation or hydroxylation reaction. The dried fluidized material is led again via line 16 to the fluidized reactor.

The waste gas which for environmental reasons should contain little carbon monoxide goes via line 8 into the cyclone 9 where entrained solids are separated. These separated solids are led via line 10 likewise to the wash container 13 and freed of catalyst. The waste gas after a further purification, for example, through a filter or wash 12, is withdrawn.

EXAMPLE 1

The experiment was carried out continuously over a time of 5 days.

The fluidized reactor (height 2,400 mm, diameter 150 mm, Cr-Ni-steel) was surrounded by a salt bath (nitrite-nitrate melt as mentioned above) which first serves for heating and later in the operation for cooling and the reactor is filled with quartz sand (diameter 0.5–1.5 mm particle size).

The sodium tungstate containing distillation residue resulting from the reaction of allyl alcohol with aqueous hydrogen peroxide to form glycide (said residue containing about 20 weight % sodium hydrogen tungstate) was mixed with water in the ratio of 4–8:1 (distillation residue to water) and heated to 70°–80° C. The now pumpable mixture was fed into the reactor in the lower part thereof at a rate of about 2 kg/h while simultaneously about 8 Nm$^3$/h of air (8 normal m$^3$/h) were blown in. There was led in via a gas distributor an additional 16 Nm$^3$/h of air preheated to about 350° C.

The reactor was heated to 540° C. with the help of the salt bath. After the beginning of the combustion the temperature in the reactor was 580°–650° C. The combustion was complete so that the waste gas only had small amounts of carbon monoxide (about 0.1 volume %).

About 2–3 liters of sand were exchanged every hour. The sand carried out which contained the tungstate was washed with the corresponding amount of water so that an about 4–8% tungstate solution was obtained. The washed sand was separated, dried and returned to the reactor.

The sand and tungstate particles entrained in the waste gas were separated in a cyclone and likewise washed and the waste gas for the purpose of further purification was led over a water wash. The resulting wash water which contained small amounts of tungstate was used to dilute the starting product.

The aqueous tungstate solution can be inserted directly for the epoxidation of allyl alcohol with hydrogen peroxide.

There were present in a round flask 158 grams (2.73 mole) of allyl alcohol, 200 grams of water and 33 grams of aqueous recovered sodium tungstate solution (with 4.9% NaHWO$_4$) and heated to 45° C. With stirring there were dropped in 97 grams (1 mole) of a 35.6% hydrogen peroxide within 10 minutes. After three hours the hydrogen peroxide had reacted quantitatively. The glycide reaction yield amounted to 85% of theory based on the hydrogen peroxide.

EXAMPLE 2 (Comparison Example With Fresh Tungstate Solution)

There were present in a 1 liter three-necked flask equipped with a stirrer, dropped funnel, thermometer and reflux condenser 158 grams of allyl alcohol and 200 grams of water. 1.5 grams of HaHWO$_4$ were dissolved in 33 ml of water and added. The solution was heated to 45° C. With stirring there were dropped in within 10 minutes 97 grams of 35.6% aqueous hydrogen peroxide. After 3 hours the hydrogen peroxide reaction was quantitative. The glycide reaction yield was 86% of theory, based on the hydrogen peroxide.

EXAMPLE 3

In place of allyl alcohol in Examples 1 and 2 there were also employed crotyl alcohol of methallyl alcohol. In Table 1 the corresponding data are set forth. The reaction conditions were the same as in Examples 1 and 2.

TABLE I

| | Epoxide Yield (%) | | |
|---|---|---|---|
| | Fresh Catalyst | Returned Catalyst | Epoxide Produced |
| crotyl alcohol | 83.2 | 82.5 | 2,3-epoxybutanol-1 |
| methallyl alcohol | 55.5 | 54.7 | 1,2-epoxy-2-methyl-propanol-3 |

EXAMPLE 4

This example was analogous to Examples 1 and 2 but in place of sodium tungstate (NaHWO$_4$) there was added NaHMoO$_4$. There were present in a three necked flask equipped with a stirrer, inner thermometer, condenser and dropped funnel 58 grams (1 mole) of allyl alcohol and 3 grams of NaHMoO$_4$ dissolved in 74 ml of water and heated to 60° C. 102 grams (1.1 moles) of 36.7% aqueous H$_2$O$_2$ were dropped in inside 1 hour. After 4 hours the H$_2$O$_2$ was quantitatively reacted. The glycerine yield amounted to 70%. Using the recovered molybdenum catalyst in an analogous manner to Example 1 the glycerine yield was 67%.

EXAMPLE 5

In place of tungsten in Examples 1 and 2 there was used vanadium (Na$_2$HVO$_4$+NaH$_2$VO$_4$). The molar amounts were the same. The reaction temperature was 60° C., the reaction time 24 hours. The glycerine yield based on the H$_2$O$_2$ employed amounted to 20% with fresh catalyst and to 22% with recovered catalyst.

The concentration of the hydrogen peroxide for epoxidation of hydroxylation is not critical, preferably commercial concentrations are employed (in weight %).

Referring to FIG. 2 in like manner if the distillation residue is not pumpable it is brought into pumpable condition.

Similarly the reactor is heated to the desired temperature, i.e., at least 500° C. The heating can take place in the same manner as described in connection with FIG. 1.

The distillation residue is pumped via line 101 into the lower part of reactor 106. Simultaneously air is blown in through line 102 in order to avoid an eventual clogging. The main amount of the air necessary for combustion and fluidization is led in via line 103 and is, if necessary, preheated via the heat exchanger 112.

Preferably for heating up the fluidized reactor there is employed a salt bath 105, for example the nitrite-nitrate melt mentioned above. After the starting up of the reactor the salt bath serves as a heat transfer. The excess heat of combustion can thereby by used for the production of energy, as for example, to produce steam, for example by a suitable heat exchanger 119 in the salt bath. Thus water introduced through line 118 passing through the heat exchanger 119 forms steam. The addition of the material to be fluidized takes place via line 107, the withdrawal together with the metal compounds of the catalyst via line 104.

The fluidized material which contains these metal compounds goes into a container 114 where it is washed out, for example, with water, lyes, e.g., sodium hydroxide solution, acids, e.g., hydrochloric acid or sulfuric acid or organic solvents such as aliphatic alcohols, e.g., methyl alcohol, ethyl alcohol, propyl alcohol or isopropyl alcohol, if it is intended to recover them.

The fluidized material is then separated from the solution, dried and returned via line 117 to the fluidized reactor. The waste gas which for environmental reasons should contain little carbon monoxide goes via line 108 into the cyclone 109 where entrained solids are separated. These separated solids are led via line 110 likewise to the wash container 114. The still hot gases serve to heat up the fresh air in heat exchanger 112 and is subjected to a purification to separate the fine dust, for example, by a filter or a wash 113.

The industrial advantage of this form of the process of the invention is that the entire carbon containing portion of the distillation residue in the presence of metal containing catalysts can be burned in a single step. The metal compounds of the catalyst resulting thereby are not contaminated by organic byproducts or foreign ions.

EXAMPLE 6

In the epoxidation or hydroxylation of allyl alcohol with aqueous hydrogen peroxide to glycide or glycerine in the presence of sodium tungstate (Na$_2$WO$_4$) there results a distillation residue which contains up to 20 weight % of the catalyst, while the rest is glycerine or polyglycerines, this distillation residue was mixed with water in the ratio of 4–8:1 (distillation residue to water) and heated to 70°–80° C. The now pumpable mixture was fed into the reactor in the lower part thereof (about 2 kg/h) whereby simultaneously there were blown in about 8 Nm$^3$/h of air. There was led in via a gas distributor an additional 16 Nm$^3$/h of air preheated to about 350° C.

The fluidized reactor (height 2,400 mm, diameter 150 mm, Cr-Ni-steel) was surrounded by a salt bath (the nitrite-nitrate melt set forth in Example 1) which first serves for heating and after the starting up of the reactor as a heat acceptor. The excess heat of combustion was thereby used to produce steam through use of a heat exchanger introduced into the salt bath. As fluidized material there was used quartz sand having a particle size 0.5–1.5 mm.

The reactor was heated to 540° C. with the help of the salt bath. After the beginning of the combustion the temperature in the reactor is about 580°–650° C. The burning is complete so that in the waste gas only small amounts of carbon monoxide (about 0.1 weight %) are present.

About 2–3 liters of sand were exchanged every hour. The sand carried out which contained the tungstate was washed with the corresponding amount of water so that an about 4-8% tungstate solution was obtained. The washed sand was separated off, dried and returned to the reactor.

The aqueous tungstate solution can be inserted directly for the epoxidation or hydroxylation of allyl alcohol with hydrogen peroxide.

The sand and tungstate particles extrained in the waste gas were separated off in a cyclone and likewise washed out. The still hot waste gas was used in a heat exchanger to heat the fresh air needed for the combustion. Subsequently the cooled waste gases for the purpose of further purification was led over a wash. The resulting was water which contained small amounts of tungstate was used to dilute the distillation residue.

EXAMPLE 7

In the epoxidation of cyclohexene with cumene hydroperoxide in the presence of vanadyl acetyl acetonate to 1,2-epoxycyclohexane there resulted a distillation residue which contained the vanadium compound. This distillation residue was burned in a manner analogous to that in Example 6.

The vanadium pentoxide formed was separated out on the fluidized material or in the cyclone. The vanadium pentoxide was dissolved out of the fluidized material with aqueous sodium hydroxide. The vanadium or its compounds can be recovered from this aqueous vanadate solution by customary methods. By heating the vanadium pentoxide containing fluidized material with an alcohol, for example, propanol, the vanadium pentoxide can be converted into the corresponding vanadic acid esters. In place of propanol other alkanols can be used, e.g., methanol, ethanol, isopropanol, butanol, etc.

EXAMPLE 8

In the epoxidation of propylene with tert. butyl peroxide in the presence of niobium phthalate to propylene oxide there resulted a distillation residue which contained the niobium compound. This distillation residue was burned in a manner analogous to that in Example 6. The niobium pentoxide formed thereby was separated off on the fluidized material or in the cyclone. The niobium pentoxide was dissolved out of the fluidized material with aqueous sodium hydroxide. There wash solutions were worked up according to conventional methods.

The process of the invention can comprise, consist essentially of or consist of the steps set forth.

What is claimed is:

1. In a process for the separation of a catalyst employed in the epoxidation or hydroxylation of an olefinic compound with a peroxy compound in a reactor, distilling off the epoxidized or hydroxylated product and separation of the catalyst from the distillation residue containing said catalyst and high boiling organic compounds, said catalyst being a compound of a transition metal, the improvement comprising introducing the distillation residue into a bed of fluidized inert solid particles, burning the organic compounds of said distillation residue with an oxygen containing gas while in contact with said fluidized particles and separating fluidized particles containing a compound of the metal employed in the catalyst from the waste gas of said burning.

2. The process of claim 1 wherein the catalyst is a compound of zirconium, vanadium, niobium, tantalum, chromium, molybdenum, tungsten, rhenium or uranium.

3. The process of claim 2 wherein the catalyst is a compound of vanadium, tungsten or niobium.

4. The process of claim 2 wherein the catalyst is a compound of tungsten, molybdenum or vanadium.

5. The process of claim 2 wherein the olefinic compound is allyl alcohol, cyclohexene or propylene.

6. The process of claim 2 wherein the peroxy compound is an organic peroxide, organic hydroperoxide or hydrogen peroxide.

7. The process of claim 2 wherein the inert solid particles are quartz sand, silicon carbide, highly fired alumina or highly fired clay.

8. The process of claim 2 wherein the fluidized particles have a particle size of 0.1 to 5 mm.

9. The process of claim 8 wherein the fluidized particles have a particle size of 0.5 to 1.5 mm.

10. The process of claim 2 wherein the oxygen containing gas is air.

11. The process of claim 2 wherein the burning temperature is between 500° and 1000° C. and also is not over the melting point of the inorganic compound of the metal of the catalyst formed in the burning.

12. In a process for the recovery of a catalyst employed in the epoxidation of hydroxylation of a water soluble olefinic compound with hydrogen peroxide in a reactor, distilling off the epoxidized or hydroxylated product and separation of the catalyst from the distillation residue, containing said catalyst, and high boiling organic compounds, said catalyst being a water soluble compound of vanadium, molybdenum or tungsten, the improvement comprising introducing the distillation residue into a bed of fluidized inert, water insoluble solid particles, burning the organic components of said distillation residue with an oxygen containing gas at a temperature below the melting point of said catalyst while in contact with said fluidized particles, removing a portion of said inert solid particles containing said water soluble compound from the burning zone, dissolving said water soluble catalyst compound in water and separating the aqueous solution from said inert solid particles.

13. The process of claim 1 including the step of returning the aqueous solution of water soluble catalyst to the reactor for use in the epoxidation or hydroxylation of a water soluble olefinic compound.

14. The process of claim 1 wherein the oxygen containing gas is air.

15. The process of claim 1 wherein the oxygen containing gas is pure oxygen.

16. The process of claim 1 wherein the catalyst is an alkyl metal vanadate, molybdate or tungstate.

17. The process of claim 16 wherein the catalyst is a sodium tungstate.

18. The process of claim 1 wherein the water soluble olefinic compound is allyl alcohol, crotyl alcohol, methallyl alcohol or cyclopentenol-3.

19. The process of claim 1 wherein the water soluble olefinic compound is allyl alcohol.

20. The process of claim 1 wherein the inert solid particles are quartz sand, silicon carbide, highly fired alumina or highly fired clay.

21. The process of claim 1 wherein the fluidized particles have a particle size of 0.1 to 5 mm.

22. The process of claim 21 wherein the fluidized particles have a particle size of 0.5 to 1.5 mm.

23. The process of claim 1 wherein the burning temperature is between 500° and 1000° C.

24. The process of claim 1 wherein the waste gas produced in the burning and containing entrained solid particles comprising said inert solid particles and water soluble catalyst is passed to a solids separator to separate the waste gas from the solids and the water soluble catalyst portion of the entrained solids is dissolved in water and the aqueous solution thus produced separated from the inert solid particles.

25. The process of claim 24 comprising returning to the reactor both the aqueous solution of catalyst obtained from the solids separator and from the portion of inert solids particles removed from the fluidized bed for use in the epoxidation or hydroxylation of a water soluble olefinic compound.

26. The process of claim 24 wherein the solids separator is a cyclone and the process comprises passing the waste gas containing fine dust not separated in the cyclone to a water containing washer and thereby dissolving the catalyst portion of the fine dust in water.

27. The process of claim 24 wherein the solids separator is a cyclone and the process comprises filtering the waste gas containing fine dust after the cyclone to separate the fine dust from the waste gas.

28. The process of claim 1 wherein the catalyst is a sodium tungstate and there is employed sufficient water in dissolving the catalyst from the inert water insoluble particles that there is obtained a 4 to 8 weight % catalyst solution and then returning this solution to the reactor for use in the epoxidation or hydroxylation of a water soluble olefinic compound.

* * * * *